(12) United States Patent
Hayashi

(10) Patent No.: US 11,707,419 B2
(45) Date of Patent: Jul. 25, 2023

(54) COMPOSITE PARTICLES INCLUDING ANIONIC POLYMER AND CATIONIC POLYMER OR PEPTIDE, AND METHOD FOR PRODUCING COMPOSITE PARTICLES

(71) Applicant: POLA CHEMICAL INDUSTRIES, INC., Shizuoka (JP)

(72) Inventor: Ryota Hayashi, Kanagawa (JP)

(73) Assignee: POLA CHEMICAL INDUSTRIES, INC., Shizuoka (JP)

( * ) Notice: Subject to any disclaimer, the term of this patent is extended or adjusted under 35 U.S.C. 154(b) by 0 days.

(21) Appl. No.: 16/340,350

(22) PCT Filed: Oct. 4, 2017

(86) PCT No.: PCT/JP2017/036146
§ 371 (c)(1),
(2) Date: Apr. 8, 2019

(87) PCT Pub. No.: WO2018/074237
PCT Pub. Date: Apr. 26, 2018

(65) Prior Publication Data
US 2019/0231655 A1    Aug. 1, 2019

(30) Foreign Application Priority Data

Oct. 17, 2016  (JP) .............................. JP2016-203809
Oct. 18, 2016  (JP) .............................. JP2016-204693

(51) Int. Cl.
*A61K 8/02*    (2006.01)
*A61K 8/73*    (2006.01)
(Continued)

(52) U.S. Cl.
CPC .............. *A61K 8/0241* (2013.01); *A61K 8/64* (2013.01); *A61K 8/65* (2013.01); *A61K 8/73* (2013.01);
(Continued)

(58) Field of Classification Search
None
See application file for complete search history.

(56) References Cited

U.S. PATENT DOCUMENTS

2010/0197904 A1 *   8/2010   Asaoka ............... C08B 37/0072
                                                                536/53
2011/0014235 A1 *   1/2011   Berninger ............ A61K 31/575
                                                                424/246.1
(Continued)

FOREIGN PATENT DOCUMENTS

CN      101466408 A      6/2009
CN      101715457 A      5/2010
(Continued)

OTHER PUBLICATIONS

Szarpak, Biomacromolecules, 11, 3, 2010 (Year: 2010).*
(Continued)

*Primary Examiner* — Susan T Tran
*Assistant Examiner* — William Craigo
(74) *Attorney, Agent, or Firm* — Calfee Halter & Griswold LLP

(57) ABSTRACT

A first problem is to provide a novel technique for forming hyaluronan into particles. Further, a second problem is to provide a novel technique suitable for production of a composite particle containing an anionic polymer and a peptide.
Means for solving the first problem is a composite particle containing an anionic polymer, and a cationic polymer (except for chitosan) having a degree of cationization of 0.2 or more. Means for solving the second problem is to mix an anionic polymer and a peptide in an aqueous solvent having a pH of 5 or less.

3 Claims, 1 Drawing Sheet

— SODIUM HYALURONATE-POLYLYSINE (PRIMARY)
═ SODIUM HYALURONATE-PROTAMINE (PRIMARY)
⋯ SODIUM HYALURONATE-CATIONIZED CELLULOSE (QUATERNARY)
— — SODIUM HYALURONATE-DIALLYLDIMETHYLAMINE HYDROCHLORIDE POLYMER (QUATERNARY)

(51) Int. Cl.
- *A61Q 19/00* (2006.01)
- *A61K 8/64* (2006.01)
- *A61K 8/65* (2006.01)
- *A61K 8/88* (2006.01)
- *A61K 8/81* (2006.01)
- *A61K 9/10* (2006.01)
- *A61P 43/00* (2006.01)
- *A61K 31/728* (2006.01)
- *A61P 17/00* (2006.01)
- *A61K 38/02* (2006.01)

(52) U.S. Cl.
CPC .............. *A61K 8/735* (2013.01); *A61K 8/81* (2013.01); *A61K 8/88* (2013.01); *A61K 9/10* (2013.01); *A61K 31/728* (2013.01); *A61K 38/02* (2013.01); *A61P 17/00* (2018.01); *A61P 43/00* (2018.01); *A61Q 19/00* (2013.01)

(56) References Cited

U.S. PATENT DOCUMENTS

| | | | |
|---|---|---|---|
| 2011/0256059 A1* | 10/2011 | Sanchez Barreiro | A61K 9/5161 424/9.1 |
| 2013/0052127 A1 | 2/2013 | Sasaki et al. | |
| 2016/0206752 A1 | 7/2016 | Izaki et al. | |

FOREIGN PATENT DOCUMENTS

| | | | |
|---|---|---|---|
| CN | 102858367 A | | 1/2013 |
| JP | 2007520424 | | 7/2007 |
| JP | 2008533108 | | 8/2008 |
| JP | 2009514860 A | | 4/2009 |
| JP | 2009537604 | | 10/2009 |
| JP | 2010540411 A | | 12/2010 |
| JP | 2012504568 A | | 2/2012 |
| JP | 2012506900 A | | 3/2012 |
| JP | 2014091708 A | | 5/2014 |
| JP | 2014091708 A | * | 5/2014 |
| JP | 2014114272 A | | 6/2014 |
| JP | 2017066046 A | | 4/2017 |
| WO | 2007132873 A1 | | 11/2007 |
| WO | 2010037566 A1 | | 4/2010 |
| WO | 2011105520 A1 | | 9/2011 |
| WO | 2015064591 A1 | | 5/2015 |
| WO | 2015189387 A1 | | 12/2015 |

OTHER PUBLICATIONS

Kayitmazer, Soft Matter, 11, 2015 (Year: 2015).*

English Translation of International Search Report from International Application No. PCT/JP2017/036146 dated Dec. 19, 2017 (7 pages).

Szarpak, Anna, et al., Designing Hyaluronic Acid-Based Layer-by-Layer Capsules as a Carrier for Intracellular Drug Delivery, Biomacromolecules, Jan. 28, 2010, vol. 11, No. 3, pp. 713-720.

Zhang, Pan, et al., Polyamine/salt-assembled micro spheres coated with hyaluronic acid for targeting and pH sensing, Colloids and Surfaces B: Biointerfaces, Mar. 3, 2016, vol. 142, pp. 223-229.

Gunji, Shutaro, "Drug Delivery to CD44-postive Cancer by Hyaluronicacid-Cationized Gelatin", Nov. 21, 2011, vol. 33, pp. 69, (Annual Meeting of the Japanese Society for Biomaterials), non-official translation.

Kayitmazer et al., "Complex Coacervation of Hyaluronic Acid and Chitosan: Effects of PH, Ionic Strength, Charge Destiny, Chain Length and the Charge Ratio", Soft Matter, 2015, 11, pp. 8605-8612.

Varvaresou et al., Efficacy and Tolerance Study of Oligopeptide with Potential Anti-Aging Activity, Journal of Cosmetics, Dermalogical Sciences and Applications, 2011, pp. 133-140.

Leon-Lopez et al., "Hydrolysed Collagen from Sheepskins as a Source of Functional Peptides with Antioxidant Activity" International Journal of Molecular Sciences, published Aug. 13, 2009, 17 pages.

* cited by examiner ature thereof; and b) chitosan or a derivative thereof, and are characterized in that the molecular weight of the chitosan or the derivative thereof is less than 90 kDa. Further, in Patent Literature 4, a system including a nucleic acid as a biologically active molecule, and a system including a tripolyphosphate as a reticulating agent are described.

COMPOSITE PARTICLES INCLUDING ANIONIC POLYMER AND CATIONIC POLYMER OR PEPTIDE, AND METHOD FOR PRODUCING COMPOSITE PARTICLES

CROSS-REFERENCE TO RELATED APPLICATIONS

This application is a 371 of PCT Application No. PCT/JP2017/036146 filed on Oct. 4, 2017, which claim priority to Japanese Application No. 2016-203809 filed on Oct. 17, 2016, and Japanese Application No. 2016-204693 filed on Oct. 18, 2016, the contents of which are hereby incorporated by reference as if recited in their entirety.

TECHNICAL FIELD

The present invention relates to nanoparticles capable of being utilized as a raw material for a skin external preparation, and a method for producing the nanoparticles.

BACKGROUND ART

In order to deliver an active component of a skin external preparation into a layer of corneocytes, conventionally, the following points have been taken into consideration as problems.

A layer of horny layer cells of the skin has a barrier function in order to prevent the invasion of foreign matter from the outside, and therefore an active component hardly reaches the inside of the layer of horny layer cells. In particular, in case where the active component is a polymer compound, the active component hardly permeates the layer of horny layer cells because of the low permeability of the polymer compound, and therefore, the active component remains on the skin surface.

In such a circumstance, as a carrier for delivering an active component into the layer of horny layer cells, nanoparticles have been developed.

In Patent Literature 1, there is a description of a freeze-dried product of a complex that contains a nucleic acid, an oligonucleic acid or a derivative thereof, a cationic polymer or a cationic lipid or a mass containing the same, and an anionic polymer.

In Patent Literature 2, there is a description of a method for obtaining nanoparticles for administration of an activity component having a diameter of less than 1 μm, comprising: a) preparing an aqueous solution of a salt of hyaluronan; b) preparing an aqueous solution of a cationic polymer; c) adding a salt of polyanion into the aqueous solution of a salt of hyaluronan; and d) mixing the solutions obtained in b) and c) under stirring to spontaneously obtain nanoparticles, wherein the activity component is dissolved in one of the solutions obtained in a), b) and c), or in a suspension of the nanoparticles obtained in d) to be adsorbed on the nanoparticles.

In Patent Literature 3, there is a description of a system comprising nanoparticles for the release of biologically active molecules, wherein the nanoparticles include a conjugate containing a) at least 50% by weight of chitosan or a derivative of chitosan, and b) less than 50% by weight of polyethylene glycol (PEG) or a derivative of PEG, and both components a) and b) are covalently bound through the chitosan amino groups, and characterized in that said nanoparticles are crosslinked by means of a crosslinking agent.

In Patent Literature 4, there is a description of a system for the release of biologically active molecules, comprising nanoparticles with an average size of less than 1 micrometer, wherein the nanoparticles include: a) hyaluronan or a salt thereof; and b) chitosan or a derivative thereof, and are characterized in that the molecular weight of the chitosan or the derivative thereof is less than 90 kDa. Further, in Patent Literature 4, a system including a nucleic acid as a biologically active molecule, and a system including a tripolyphosphate as a reticulating agent are described.

In Patent Literature 5, a binary complex containing hyaluronan and chitosan, and a ternary complex further containing an anionic polymer in addition to hyaluronan and chitosan are described.

PRIOR ART DOCUMENTS

Patent Literature

Patent Literature 1: WO 2007/132873
Patent Literature 2: JP-A 2007-520424
Patent Literature 3: JP-A 2008-533108
Patent Literature 4: JP-A 2009-537604
Patent Literature 5: JP-A 2014-114272

DISCLOSURE OF THE INVENTION

Problems to be Solved by the Invention

As described in Patent Literature 5, hyaluronan easily form a composite particle with chitosan. However, it has been unknown what kind of polymer having what kinds of properties can form a composite particle with hyaluronan under what kinds of conditions, in addition to the chitosan.

In view of this, an object to be solved by a first aspect of the present invention is to provide a novel technique for forming hyaluronan into particles.

In addition, as described in Patent Literature 5, hyaluronan and chitosan are easily form a composite particle in the vicinity of the neutrality (pH 6.5).

In the course of various studies on a polymer capable of forming a composite particle with an anionic polymer, the present inventors have found that hyaluronan and a peptide hardly forma composite particle having a small particle diameter under such a neutral condition.

In view of this, an object to be solved by a second aspect of the present invention is to provide a novel technique suitable for the production of a composite particle containing an anionic polymer and a peptide.

Means to Solve the Problems

First Aspect of the Invention

As a result of keen studies, the present inventors have found that the degree of cationization is important as a property of a cationic polymer capable of forming a composite particle with hyaluronan, and thus have completed the present invention.

That is, the first aspect of the present invention to solve the above problem is a composite particle including an anionic polymer, and a cationic polymer (except for chitosan) having a degree of cationization of 0.2 or more.

The composite particle of the present invention is useful as a carrier for delivering an active component into the skin.

In a preferred embodiment of the present invention, the anionic polymer is hyaluronan and/or polyglutamic acid.

The composite particle of the present invention in such an embodiment can deliver hyaluronan and polyglutamic acid that are moisturizing components to the inside of the skin.

In a preferred embodiment of the present invention, the cationic polymer is an allyl-based amine polymer and/or a cationized polysaccharide.

By using these cationic polymers, the stability of the composite particle can be improved.

In a preferred embodiment of the present invention, the cationic polymer is a primary to tertiary amine.

The composite particle of the present invention, which includes a cationic polymer being a primary to tertiary amine, has a property of permeating the inside of the skin and then disintegrating. Therefore, the composite particle of the present invention in such an embodiment can introduce an anionic polymer in a non-aggregation state to the inside of the skin, although the anionic polymer cannot originally permeate the inside of the skin.

In a preferred embodiment of the present invention, the cationic polymer is a peptide.

By using a peptide, the stability of the composite particle can be improved.

The present invention also relates to a composition for skin external application including the composite particle described above.

The composition for skin external application of the present invention enables the anionic polymer to permeate the inside of the skin.

The present invention also relates to a method for producing the composite particle described above. That is, the production method of the present invention is characterized by mixing an anionic polymer, and a cationic polymer (except for chitosan) having a degree of cationization of 0.2 or more, in an aqueous solvent.

According to the present invention, the composite particle described above can be easily produced.

In a preferred embodiment of the present invention, it is characterized in that an anionic polymer aqueous solution (A), and an aqueous solution of the cationic polymer (B) are separately prepared, and these aqueous solutions are mixed with each other.

In this way, by taking such an embodiment in which the aqueous solutions of (A) and (B) are separately prepared, aggregation of composite particles can be prevented.

In addition, the concentration of the anionic polymer in the aqueous solution (A) described above is preferably 1.7 mM or less.

Further, the concentration of the cationic polymers in total in the aqueous solution (B) described above is preferably 1.7 mM or less.

By setting the concentrations of the polymers in the aqueous solutions (A) and (B) to be in the ranges described above, respectively, composite particles that hardly aggregate can be produced.

The present invention also relates to a composite particle produced by the production method described above.

The composite particle of the present invention is excellent in the stability.

Second Aspect of the Invention

Further, as a result of keen studies, the present inventors have found that by mixing hyaluronan and a peptide in an aqueous solvent in an acidic region of pH 5 or less, a fine composite particle can be produced.

That is, the second aspect of the present invention to solve the above problem is a method for producing a composite particle containing an anionic polymer and a peptide, which is characterized by mixing an anionic polymer and a peptide in an aqueous solvent having a pH of 5 or less.

According to the production method of the present invention, a composite particle that contains an anionic polymer and a peptide and has a relatively small particle diameter, can be produced.

In a preferred embodiment of the present invention, the anionic polymer is hyaluronan.

The present invention is preferably applied to the production of a composite particle containing hyaluronan.

It is difficult for an anionic polymer and a peptide containing acidic and/or neutral amino acid residues to form a composite particle in the vicinity of the neutrality.

Therefore, the present invention is preferably applied to a peptide containing acidic and/or neutral amino acid residues.

In a preferred embodiment of the present invention, the peptide is one kind or two or more kinds selected from the group consisting of a water-soluble collagen, oligopeptide-20, and polylysine.

The present invention is preferably applied to the production of a composite particle containing the peptide having a useful effect on the human body.

In a preferred embodiment of the present invention, when the peptide is a water-soluble collagen, the pH of the aqueous solvent is set to 3 or less.

By taking such an embodiment, a composite particle having a small particle diameter can be produced.

In a preferred embodiment of the present invention, when the peptide is oligopeptide-20, the pH of the aqueous solvent is set to 3.5 or less.

By taking such an embodiment, a composite particle having a small particle diameter can be produced.

In a preferred embodiment of the present invention, when the peptide is polylysine, the pH of the aqueous solvent is set to 4.4 or less.

By taking such an embodiment, a composite particle having a small particle diameter can be produced.

In a preferred embodiment of the present invention, an aqueous solution of the anionic polymer, and an aqueous solution of the peptide are separately prepared, and these aqueous solutions are mixed with each other.

In this way, by taking such an embodiment in which the aqueous solution of the anionic polymer and the aqueous solution of the peptide are separately prepared, aggregation of composite particles can be prevented.

The present invention also relates to a method for producing a composite particle-containing composition that contains the composite particle produced by the production method described above.

That is, the method for producing a composite particle-containing composition of the present invention includes a step of producing a composite particle by the production method described above, and then mixing the composite particle with an aqueous solvent and other components, and is characterized in that a pH of a composition after mixing may be different from a pH of the aqueous solvent.

The composite particle produced by the production method described above does not disappear even if the pH varies thereafter. Therefore, according to the present invention, a composite particle-containing composition can be easily produced.

Further, the present invention also relates to a composite particle including an anionic polymer and a peptide, and the composite particle is characterized in that the peptide is one kind or two or more kinds selected from the group consisting of a water-soluble collagen, oligopeptide-20, and polylysine, and the composite particle has a particle diameter of 500 nm or less.

The composite particle of the present invention can be used for the purpose of allowing an anionic polymer and a peptide to permeate the inside of the skin.

In a preferred embodiment of the present invention, the anionic polymer is hyaluronan.

According to the composite particle of the present invention, hyaluronan can be introduced to the inside of the skin.

Advantageous Effects of Invention

The composite particle of the first aspect of the present invention enables the anionic polymer to permeate the inside of the skin. Further, according to the method for producing a composite particle of the present invention, the composite particle described above can be easily produced.

According to the production method of the second aspect of the present invention, a composite particle having a relatively small particle diameter, which contains an anionic polymer and a peptide, can be provided.

Further, according to the composite particle of the present invention, the anionic polymer and the peptide can permeate the inside of the skin.

FIRST ASPECT OF THE INVENTION

Figure 1:
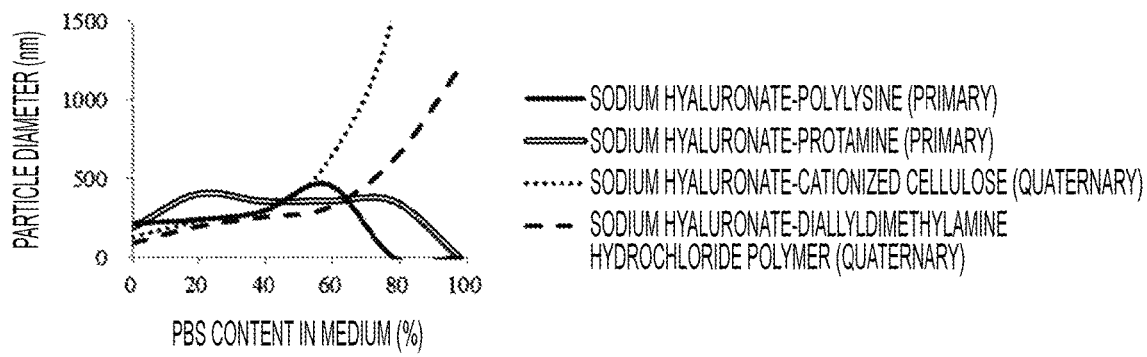
FIG. 1 is a graph showing the relationship between the addition amount of PBS and the particle diameter of a composite particle.

<1> Composite Particle
(1) Anionic Polymer

The composite particle according to the present invention contains an anionic polymer as a required element. The anionic polymer is not limited as long as it does not harm the human body, and examples of the anionic polymer suitably include an anionic polyamino acid such as polyglutamic acid, and polyaspartic acid, an anionic polysaccharide such as agar, hyaluronan, chondroitin sulfate, dextran sulfate, heparan sulfate, dermatan sulfate, fucoidan, keratan sulfate, heparin, carrageenan, succinoglucan, gum arabic, xanthane gum, algic acid, pectin, and carboxymethyl cellulose, polyacrylic acid, and a salt thereof. In particular, hyaluronan, polyglutamic acid, and a salt thereof can be suitably mentioned.

As the anionic polymer, a commercially available product can be used.

As the salt forming a hyaluronan salt and a polyglutamate salt, sodium, potassium, calcium, ammonium, magnesium, a basic amino acid salt, or the like can be mentioned.

The molecular weight of the anionic polymer to be used in the present invention is not limited, and is preferably 100 to 100000 kDa, and more preferably 200 to 50000 kDa.

More specifically, in case where hyaluronan or a salt thereof is used as the anionic polymer, hyaluronan or a salt thereof, which has a molecular weight of preferably 100 to 2000 kDa, and furthermore preferably 200 to 1500 kDa, can be used.

Further, in case where polyglutamic acid or a salt thereof is used as the anionic polymer, polyglutamic acid or a salt thereof, which has a molecular weight of preferably 500 to 30000 kDa, more preferably 1000 to 20000 kDa, and furthermore preferably 1500 to 15000 kDa, can be used.

The degree of anionization of an anionic polymer is not particularly limited, and from the viewpoint of promoting the formation of a composite particle with a cationic polymer, the lower limit is preferably 0.1 or more, and more preferably 0.2 or more.

On the other hand, from the viewpoint of forming the composite particle with a cationic polymer, there is no particular upper limitation on the degree of anionization of an anionic polymer. As a guide, an anionic polymer having a degree of anionization of 2 or less can be used.

In this regard, the expression "degree of anionization" is referred to a value that can be obtained by calculation in accordance with the following equation.

{(The number of anionic functional groups contained in a polymer)−(The number of cationic functional groups contained in the polymer)}/ The total amount of monomers constituting the polymer (2) Cationic Polymer In the present invention, the expression "cationic polymer" is referred to a polymer showing cationicity at least in water, and includes also an amphoteric polymer that shows cationicity as a whole.

In the present invention, a polymer having a degree of cationization of 0.2 or more is used. By using such a cationic polymer, a composite particle can be easily formed with an anionic polymer.

On the other hand, from the viewpoint of forming a composite particle with an anionic polymer, there is no particular upper limitation on the degree of cationization of a cationic polymer. As a guide, a cationic polymer having a degree of cationization of 2 or less can be used.

In this regard, the expression "degree of cationization" is referred to a value that can be obtained by calculation in accordance with the following equation.

{(The number of cationic functional groups contained in a polymer)−(The number of anionic functional groups contained in the polymer)}/ The total amount of monomers constituting the polymer The cationic polymer to be used in the present invention may be a natural product or a synthetic product as long as it has a cationic functional group.

Examples of the cationic functional group to be contained in a cationic polymer include an amino group, a guanidino group, and an imino group. The cationic polymer of the present invention contains these groups in the side chain or the main chain of the polymer.

Examples of the anionic polymer include a cationized polysaccharide, an allyl-based amine polymer, and an amino group-containing (meth)acrylic acid polymer, and in particular, a cationized polysaccharide, and an allyl-based amine polymer can be preferably mentioned.

Examples of the cationized polysaccharide include a cationized cellulose, a cationized guar gum, and a cationized starch.

The allyl-based amine polymer is a polymer obtained by polymerizing monomers having an allyl group and an amino group by allyl polymerization. The number of the allyl groups possessed by a monomer is not particularly limited, and is preferably 1 or 2.

Examples of the allyl-based amine polymer include an allylamine hydrochloride polymer, an allylamine amide sulfate polymer, an allylamine hydrochloride-diallylamine hydrochloride copolymer, an allylamine acetate-diallylamine acetate copolymer, an allylamine hydrochloride-dialkylallylamine hydrochloride copolymer, a partially alkoxycarbonylated allylamine polymer, a partially alkylcarbonylated allylamine acetate polymer, a partially urea polyallylamine polymer, a diallylamine hydrochloride polymer, an alkyldiallylamine hydrochloride polymer, an alkyldiallylamine amide sulfate polymer, an alkyldiallylamine acetate polymer, a diallyldimethylammonium chloride polymer, a diallylmethylethylammonium ethylsulfate polymer, a diallylamine hydrochloride-sulfur dioxide copolymer, a diallylamine acetate-sulfur dioxide copolymer, a diallylmethylethylammonium ethylsulfate-sulfur dioxide copolymer, an alkyldiallylamine hydrochloride-sulfur dioxide copolymer, a diallyldialkylammonium chloride-sulfur dioxide copolymer, and a diallyldialkylammonium chloride-acrylamide copolymer.

The amino group-containing (meth)acrylic acid polymer is not particularly limited as long as it has a structure in which a side chain structure containing an amino group is bonded to a carboxyl group moiety of a (meth)acrylic acid polymer by an ester bond or an amide bond. The side chain structure may be linear or branched. The amino group contained in the side chain may be any one of the primary to tertiary amino groups, or may be in a form of a quaternary ammonium.

In a preferred embodiment of the present invention, a cationic polymer that is a primary to tertiary amine is used. In a more preferred embodiment, an allyl-based amine polymer that is a primary to tertiary amine is used.

Specific examples of the primary to tertiary allyl-based amine polymer include an allylamine hydrochloride polymer, an allylamine amide sulfate polymer, an allylamine hydrochloride-diallylamine hydrochloride copolymer, an allylamine acetate-diallylamine acetate copolymer, an allylamine hydrochloride-dialkylallylamine hydrochloride copolymer, a partially alkoxycarbonylated allylamine polymer, a partially alkylcarbonylated allylamine acetate polymer, a partially urea polyallylamine polymer, a diallylamine hydrochloride polymer, an alkyldiallylamine hydrochloride polymer, an alkyldiallylamine amide sulfate polymer, an alkyldiallylamine acetate polymer, a diallylamine hydrochloride-sulfur dioxide copolymer, a diallylamine acetate-sulfur dioxide copolymer, and an alkyldiallylamine hydrochloride-sulfur dioxide copolymer.

As the amphoteric polymer that can be classified into a cationic polymer because of being cationic as a whole, an acetic acid amphoteric compound of a dialkylaminoethyl methacrylate polymer, a methacryloyl ethyl betain/methacrylate copolymer, an octylacrylamide acrylate/hydroxypropyl acrylate/butylaminoethyl methacrylate copolymer, a dimethyldiallylammonium chloride/acrylic acid copolymer, a dimethyldiallylammonium chloride/acrylic acid/acrylamide copolymer, and a methacrylamide propyl trimethyl ammonium chloride/acrylic acid/methyl acrylate copolymer can be preferably mentioned.

Further, as the cationic polymer, it is preferred to use a peptide showing cationicity as a whole.

The kind of the peptide is not particularly limited, and a basic peptide having a ratio of basic amino acid residues of preferably 70% or more, more preferably 80% or more, furthermore preferably 90% or more, and still furthermore preferably 99% or more, relative to the total amino acid residues is preferably used.

In particular, a basic peptide constituted only of basic amino acid residues can be preferably mentioned.

As the basic peptide, a peptide constituted of arginine and lysine can be particularly suitably mentioned.

Specifically, polylysine, or polyarginine is preferably used.

Further, as the peptide, either a peptide constituted of a single amino acid residue, or a peptide constituted of two or more kinds of amino acid residues may be used.

(3) Composite Particle

The composite particle according to the present invention contains the above-described anionic polymer and cationic polymer as essential components.

The mass ratio of the anionic polymer to the cationic polymer in a composite particle is preferably 10:1 to 1:10, more preferably 5:1 to 5:1, furthermore preferably 2:1 to 1:2, and still furthermore preferably 1.5:1 to 1:1.5, on a charged amount basis.

The composite particle may contain optional components other than the above-described essential components, and the total content of the essential components in the entire composite particle is preferably 50% by mass or more, more preferably 70% by mass or more, furthermore preferably 90% by mass or more, and still more preferably 99% by mass or more.

The average particle diameter of the composite particle is preferably 1000 nm or less, more preferably 500 nm or less, furthermore preferably 300 nm or less, and still more preferably 100 nm or less.

(4) Method for Producing Composite Particle

The method for producing the composite particle described above is not particularly limited, and the composite particle is preferably produced by the production method of the present invention. Hereinafter, specific embodiments of the method for producing a composite particle according to the present invention will be described.

The production method of the present invention is characterized by mixing an anionic polymer, and a cationic polymer (except for chitosan) having a degree of cationization of 0.2 or more, in an aqueous solvent.

According to the production method of the present invention, a composite particle can be produced by a simple operation of mixing polymers that are essential components in an aqueous solvent.

The expression "aqueous solvent" is referred to water (for example, purified water, ion exchanged water, tap water, or the like), or an aqueous solution of a water-soluble component. As the water-soluble component, any component can be used without particular limitation as long as it does not impair the effects of the present invention, and examples of the water-soluble component include powders that are usually mixed in a cosmetic or a quasi drug, and an additive such as a moisturizer, a thickener, or an antiseptic agent. In this regard, in case where a water-soluble component having a high-melting point is mixed in water, the water-soluble component can be heated and homogeneously dissolved in water in advance, and after dissolving the water-soluble component in water, it is preferred that the temperature of the aqueous solution is returned to around the room temperature, and then the aqueous solution is used for producing a composite particle.

It is preferred to take an embodiment in which an anionic polymer aqueous solution and a cationic polymer aqueous solution are separately prepared in advance, and then these aqueous solutions are mixed with each other.

By taking such an embodiment in which the polymer aqueous solutions thus separately prepared are mixed with each other, aggregation of composite particles can be prevented.

In case where an anionic polymer aqueous solution is prepared in advance, the concentration of the anionic polymer in the aqueous solution is preferably 1.7 mM or less, more preferably 1 mM or less, and furthermore preferably 0.9 mM or less.

With the adjustment to such a concentration, unnecessary aggregation of particles can be avoided when the anionic polymer aqueous solution is mixed with a cationic polymer aqueous solution in the subsequent step.

In case where a cationic polymer aqueous solution is prepared in advance, the concentration of each of the polymers in the aqueous solution is preferably 1.7 mM or less, more preferably 1 mM or less, and furthermore preferably 0.9 mM or less.

With the adjustment to such a concentration, unnecessary aggregation of particles can be avoided when the cationic polymer aqueous solution is mixed with an anionic polymer aqueous solution in the subsequent step.

The concentration of the anionic polymer to the solution after mixing is preferably 0.9 mM or less, and more preferably 0.5 mM or less.

The concentration of the cationic polymer to the solution after mixing is preferably 0.9 mM or less, and more preferably 0.5 mM or less.

Examples of the mixing method include a method of mixing respective solutions at one time, and a method of adding one solution dropwise into the other solution. In any case, it is preferred to perform the mixing while stirring the solutions from the viewpoint of avoiding the aggregation.

The composite particle produced in this way is preferably made in a form of a composition for skin external application with the combination of an optional component. The composition for skin external application may be in any form of a medicament, a quasi drug, and a cosmetic.

Examples of the optional component include anionic surfactants such as a fatty acid soap (sodium laurate, sodium palmitate, or the like), potassium lauryl sulfate, and alkyl sulfate triethanolamine ether; cationic surfactants such as stearyltrimethylammonium chloride, benzalkonium chloride, and lauryl amine oxide; amphoteric surfactants such as an imidazoline-based amphoteric surfactant (2-cocoyl-2-imidazolinium hydroxide-1-carboxyethyloxy 2 sodium salt, or the like), a betain-based surfactant (alkyl betaine, amidobetaine, sulfobetain, or the like), and acylmethyltaurine; nonionic surfactants such as sorbitan fatty acid esters (sorbitan monostearate, sorbitan sesquioleate, and the like), glycerin fatty acids (glyceryl monostearate, and the like), propylene glycol fatty acid esters (propylene glycol monostearate, and the like), a hydrogenated castor oil derivative, glycerin alkyl ether, POE sorbitan fatty acid esters (POE sorbitan monooleate, polyoxyethylene sorbitan monostearate, and the like), POE sorbitol fatty acid esters (POE-sorbitol monolaurate, and the like), POE glycerine fatty acid esters (POE-glycerin monoisostearate, and the like), POE fatty acid esters (polyethylene glycol monooleate, POE distearate, and the like), POE alkyl ethers (POE 2-octyldodecyl ether, and the like), POE alkyl phenyl ethers (POE nonylphenyl ether, and the like), Pluronic types, POE-POP alkyl ethers (POE-POP 2-decyltetradecyl ether, and the like), Tetronics, a POE castor oil-hydrogenated castor oil derivative (POE castor oil, POE hydrogenated castor oil, or the like), a sucrose fatty acid ester, and alkyl glucoside; moisturizing components such as sodium pyrrolidone carboxylate, lactic acid, and sodium lactate; powders such as mica, talc, kaolin, synthetic mica, calcium carbonate, magnesium carbonate, silicic anhydride (silica), aluminum oxide, and barium sulfate, which may be surface-treated; inorganic pigments such as cobalt oxide, ultramarine blue, iron blue, and zinc oxide, which may be surface-treated; a composite pigment such as an iron oxide titanium dioxide sintered body, which may be surface-treated; pearl agents such as mica titanium, pearl essence, and bismuth oxychloride, which may be surface-treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked; organic powders such as polyethylene powder, polymethyl methacrylate, nylon powder, and organopolysiloxane elastomer; lower alcohols such as ethanol, and isopropanol; vitamin A or a derivative thereof; vitamin Bs such as vitamin B6 hydrochloride, vitamin B6 tripalmitate, vitamin B6 dioctanoate, vitamin B2 or a derivative thereof, vitamin B12, and vitamin B15 or a derivative thereof; vitamin Es such as α-tocopherol, β-tocopherol, γ-tocopherol, and vitamin E acetate; vitamin Ds; and vitamins such as vitamin H, pantothenic acid, pantethine, and pyrroloquinoline quinone.

Second Aspect of the Invention

The production method of the present invention has a technical feature that is to mix an anionic polymer and a peptide in an aqueous solvent having a pH of 5 or less. Hereinafter, the elements of the present invention will be described in detail, respectively.

In an embodiment of the anionic polymer that can be used in the present invention, the description in the above-described <First aspect of the invention> can be applied as it is.

The peptide that can be used in the present invention is not limited as long as it does not harm the human body, and may be a peptide including the same kind of amino acid residues, or a peptide including multiple kinds of amino acid residues.

The peptide may be a natural product or a synthetic product, or may be a peptide obtained by degradation of a protein that is a natural product or a synthetic product. Further, a chemically-modified peptide may also be used.

Specific examples of the peptide include a water-soluble collagen, oligopeptide-24 (an EGF-like synthetic peptide, having an amino acid sequence of 13 amino acids and a molecular weight of 1271), acetyl decapeptide-3 (an FGF-like synthetic peptide), oligopeptide-34 (a TGF β-like synthetic peptide, having an amino acid sequence of 13 amino acids and a molecular weight of 1468), oligopeptide-20 (an IGF-like synthetic peptide, having an amino acid sequence of 12 amino acids and a molecular weight of 1476), polylysine, and polyarginine. In particular, a water-soluble collagen, oligopeptide-20, and polyarginine can be suitably mentioned.

In the production method of the present invention, the above-described anionic polymer and peptide are mixed with each other in an aqueous solvent.

In this regard, the expression "aqueous solvent" is referred to water (for example, purified water, ion exchanged water, tap water, or the like), or an aqueous solution of a water-soluble component. As the water-soluble component, any component can be used without particular limitation as long as it does not impair the effects of the present invention, and examples of the water-soluble component include powders that are usually mixed in a cosmetic or a quasi drug, and an additive such as a moisturizer, a thickener, or an antiseptic agent. In this regard, in case where a water-soluble component having a high-melting point is mixed in water, the water-soluble component can be heated and homogeneously dissolved in water in advance, and after dissolving the water-soluble component in water, it is preferred that the temperature of the aqueous solution is returned to around the room temperature, and then the aqueous solution is used for producing a composite particle.

The upper limit of the pH of the aqueous solvent is 5 or less, preferably 4.5 or less, and more preferably 4.2 or less.

Further, the lower limit of the pH of the aqueous solvent is not particularly limited, and is preferably 1 or more, more preferably 2 or more, and furthermore preferably 2.5 or more.

In case where a water-soluble collagen is used as the peptide to be combined with an anionic polymer, the pH of the aqueous solvent is preferably 4 or less, more preferably 3.5 or less, and furthermore preferably 3 or less.

In this case, the lower limit of the pH is not particularly limited, and is preferably 2 or more, more preferably 2.5 or more, and furthermore preferably 2.7 or more.

Further, in case where oligopeptide-20 is used as the peptide to be combined with an anionic polymer, the pH of the aqueous solvent is preferably 4.5 or less, more preferably 4 or less, and furthermore preferably 3.5 or less.

In this case, the lower limit of the pH is not particularly limited, and is preferably 2 or more, more preferably 2.5 or more, furthermore preferably 2.7 or more, and still more preferably 2.75 or more.

Furthermore, in case where polylysine is used as the peptide to be combined with an anionic polymer, the pH of the aqueous solvent is preferably 4.7 or less, more preferably 4.4 or less, and furthermore preferably 4.2 or less.

In this case, the lower limit of the pH is not particularly limited, and is preferably 2 or more, more preferably 2.5 or more, furthermore preferably 3 or more, and still more preferably 3.5 or more.

The embodiment in which an anionic polymer and a peptide are mixed with each other in an aqueous solvent is not particularly limited.

In the present invention, it is preferred to take an embodiment in which an anionic polymer aqueous solution and a peptide aqueous solution are separately prepared in advance, and then these aqueous solutions are mixed with each other.

By taking such an embodiment in which the polymer aqueous solutions thus separately prepared are mixed with each other, aggregation of composite particles can be prevented.

The pH of each of the anionic polymer aqueous solution and the peptide aqueous solution, which are to be prepared in advance, is not particularly limited, and the pH of the aqueous solvent after mixing is accepted in the range described above.

An embodiment in which an anionic polymer aqueous solution and a peptide aqueous solution, each of the aqueous solutions being prepared so as to have a desired pH in advance, are mixed with each other without particularly having a step of adjusting the pH of an aqueous solvent after mixing may be accepted.

Further, from the viewpoint of simplifying the production process, it is preferred to take an embodiment in which an anionic polymer aqueous solution and a peptide aqueous solution are mixed with each other, and then the pH of an aqueous solvent is adjusted with the addition of an acid aqueous solution.

As the acid aqueous solution for adjusting the pH of an aqueous solvent, it is not particularly limited, and an aqueous solution of an organic acid such as citric acid, phosphoric acid, malic acid, or lactic acid can be preferably mentioned.

In case where an anionic polymer aqueous solution is prepared in advance, the concentration of the anionic polymer in the aqueous solution is preferably 1.7 mM or less, more preferably 1 mM or less, and furthermore preferably 0.9 mM or less.

With the adjustment to such a concentration, unnecessary aggregation of particles can be avoided when the anionic polymer aqueous solution is mixed with a peptide in the subsequent step.

In case where a peptide aqueous solution is prepared in advance, the concentration of each of polymers in the aqueous solution is preferably 5.1 mM or less, more preferably 3 mM or less, and furthermore preferably 2.7 mM or less.

With the adjustment to such a concentration, unnecessary aggregation of particles can be avoided when the peptide aqueous solution is mixed with an anionic polymer aqueous solution in the subsequent step.

In this regard, the molar concentration of peptide referred to herein is a value calculated by setting the value obtained by multiplying the molecular weight of each of the constituent amino acids by the constitution ratio to be 1 mol.

The concentration of the anionic polymer to the solution after mixing is preferably 0.9 mM or less, and more preferably 0.5 mM or less.

The concentration of the peptide to the solution after mixing is preferably 2.7 mM or less, and more preferably 1.5 mM or less.

Examples of the mixing method include a method of mixing respective solutions at one time, and a method of adding one solution dropwise into the other solution. In any case, it is preferred to perform the mixing while stirring the solutions from the viewpoint of avoiding the aggregation.

According to the production method of the present invention, a composite particle having a particle diameter almost the same as that of or smaller, depending on the kind of the peptide, than that of the composite particle obtained by mixing an anionic polymer and a peptide in an aqueous solvent in the vicinity of neutrality can be produced.

In addition, the present invention also relates to a composite particle containing an anionic polymer and a peptide.

From the viewpoint of allowing a composite particle to permeate the inside of the skin, the particle diameter is 500 nm or less, more preferably 400 nm or less, and furthermore preferably 300 nm or less.

In this regard, the particle diameter can be measured by a light scattering method using a particle size distribution measuring device.

With respect to the anionic polymer and the peptide, which can be used for the composite particle of the present invention, the items relating to the above-described production method can be applied.

The composite particle of the present invention can be made into a composite particle-containing composition with the combination of an optional component. The present invention also relates to a method for producing a composite particle-containing composition, including a step of producing a composite particle by the production method described above, and then mixing the composite particle with an aqueous solvent and other components.

In this regard, a composite particle once formed does not disappear due to the pH fluctuations. Therefore, the pH of the mixture after mixing an aqueous solvent with other components may vary from the pH of the aqueous solvent.

The composite particle-containing composition is preferably made in a form of a composition for skin external application. The composition for skin external application may be in any form of a medicament, a quasi drug, and a cosmetic.

The composite particle may be combined with an optional component. Examples of the optional component include the components listed in the above <First aspect of the invention>.

EXAMPLES

First Aspect of the Invention

Test Example 1

Aqueous solutions of an anionic polymer and a cationic polymer, which were shown in Table 1, were separately prepared. An anionic polymer aqueous solution was prepared so as to be 0.2 mM, and a cationic polymer aqueous solution was prepared so as to be 0.2 to 2 mM (at this time, a peptide aqueous solution was prepared so as to be 0.1 to 0.2 mM).

Next, each of the cationic polymer aqueous solutions thus prepared was added dropwise into each of the anionic polymer aqueous solutions thus prepared while stirring to prepare a mixture solution. The mixture ratio of the anionic polymer aqueous solution to the cationic polymer aqueous solution was set to be 1:1.

TABLE 1

|  | Component name | Raw material example | Degree of anionization |
|---|---|---|---|
| Anionic polymer | Sodium hyaluronate | Hyaluronic acid FCH-120 | 1 |
|  | Sodium polyglutamate | AminoPGALE P | 1 |
|  |  |  | Degree of cationization* |
| Cationic polymer | Diallyldimethylamine hydrochloride polymer | ME polymer H40W | 1 |
|  | Allylamine hydrochloride polymer | PAA-HCl-3L | 1 |
|  | Diallylamine hydrochloride polymer | PAS-21CL | 1 |
|  | Methyl diallylamine hydrochloride polymer | PAS-M-1 | 1 |
|  | Cationized cellulose | Catinal HC-100 | 0.2 to 1 |
|  | Acrylamide-diallyldimethylamine hydrochloride copolymer | Merquat 2200 | 0.24 to 0.88 |
|  | Cationized starch | Sensomer CI-50 | 0.2 to 0.5 |
|  | Cationized polyvinyl alcohol | GOHSENX K-434 | 0.1 |
|  | Acrylic acid-acrylamide-diallyldimethylamine hydrochloride copolymer | Merquat PLUS 3330 | 0* |
|  | Polymethacryloyl-L-lysine | PM lysine | 0* |
|  | Arginine/lysine oligopeptide | Peptiskin | 1 to 2 |
|  | Polylysine | Polylysine 10 | 1 |

*When an anionic group was included in the polymer structure similarly to a cationic group, the ratio obtained with the subtraction of the number of the anionic groups from the number of the cationic groups was set as the degree of cationization.

Each of the prepared mixture solutions was subjected to the measurement using ELS-Z2 (manufactured by Otsuka Electronics Co., Ltd.) (dynamic light scattering method), and in case where Brownian motion was observed, it was determined that composite particles were formed. The results are shown in Table 2.

TABLE 2

|  |  |  | Anionic polymer used | |
|---|---|---|---|---|
|  | Component name | Degree of cationization* | Sodium hyaluronate | Sodium polyglutamate |
| Cationic polymer | Diallyldimethylamine hydrochloride polymer | 1 | ○ | ○ |
|  | Allylamine hydrochloride polymer | 1 | ○ | ○ |
|  | Diallylamine hydrochloride polymer | 1 | ○ | ○ |
|  | Methyl diallylamine hydrochloride polymer | 1 | ○ | ○ |

TABLE 2-continued

| Component name | Degree of cationization* | Anionic polymer used | |
| --- | --- | --- | --- |
| | | Sodium hyaluronate | Sodium polyglutamate |
| Cationized cellulose | 0.2 to 1 | ○ | ○ |
| Acrylamide-diallyldimethylamine hydrochloride copolymer | 0.24 to 0.88 | ○ | ○ |
| Cationized starch | 0.2 to 0.5 | ○ | ○ |
| Cationized polyvinyl alcohol | 0.1 | X | X |
| Acrylic acid-acrylamide-diallyldimethylamine hydrochloride copolymer | 0* | X | X |
| Polymethacryloyl-L-lysine | 0* | X | X |
| Arginine/lysine oligopeptide | 1 to 2 | ○ | ○ |
| Polylysine | 1 | ○ | ○ |

*When an anionic group was included in the polymer structure similarly to a cationic group, the ratio obtained with the subtraction of the number of the anionic groups from the number of the cationic groups was set as the degree of cationization.
○ ... Composite particles were formed
X ... Composite particles were not formed As shown in Table 2, none of the cationic polymers having a degree of cationization of less than 0.2 did not form a composite particle with both sodium hyaluronate and sodium polyglutamate. On the other hand, all of the cationic polymers having a degree of cationization of 0.2 or more formed a composite particle with both sodium hyaluronate and sodium polyglutamate.

These results indicate that with respect to the formation of a composite particle with an anionic polymer, it is important that the cationic polymer has a degree of cationization of 0.2 or more.

Test Example 2

A sodium hyaluronate aqueous solution and a diallyldimethylamine hydrochloride polymer aqueous solution were separately prepared at the concentrations shown respectively in Table 3, and then these aqueous solutions were mixed with each other to prepare each of the aqueous solutions of the composite particles of Examples 1 to 6.

The particle diameter of the composite particle formed in each of the aqueous solutions of Examples 1 to 6 was measured by using ELS-Z2 (manufactured by Otsuka Electronics Co., Ltd.) (dynamic light scattering method). The results are shown in Table 3.

TABLE 3

| | Concentration of sodium hyaluronate aqueous solution (mM) | Concentration of diallyldimethylamine hydrochloride polymer aqueous solution (mM) | Particle diameter of composite particle (nm) | Remarks |
| --- | --- | --- | --- | --- |
| Example 1 | 2.494 | 2.494 | 11561 | With aggregation |
| Example 2 | 1.995 | 1.995 | 9237.6 | With aggregation |
| Example 3 | 1.650 | 1.650 | 201.1 | With aggregation in 30 minutes |
| Example 4 | 0.825 | 0.825 | 172.7 | — |
| Example 5 | 0.500 | 0.500 | 149.8 | — |
| Example 6 | 0.200 | 0.200 | 132.5 | — |

As shown in Table 3, a particle having a remarkably large particle diameter was confirmed in each of the aqueous solutions of Examples 1 and 2, and therefore, it is recognized that the formed composite particles are aggregated.

For the aqueous solution of Example 3, the formation of a composite particle having a relatively small particle diameter was confirmed immediately after the preparation. However, the increase in the particle diameter was observed after the aqueous solution was left to stand for 30 minutes, and therefore, it is recognized that the composite particles are aggregated with the standing of the aqueous solution.

On the other hand, in each of the aqueous solutions of Examples 4 to 6, the formation of a composite particle having a small particle diameter of less than 200 nm was confirmed. Further, even when the aqueous solution was left to stand for 30 minutes or more, the increase in the particle diameter was not confirmed.

The results described above indicate that in producing a composite particle by preparing an anionic polymer aqueous solution and a cationic polymer aqueous solution separately in advance, and then mixing these aqueous solutions with each other, the anionic polymer aqueous solution is preferably prepared in a concentration of 1.7 mM or less, and the cationic polymer aqueous solution or the peptide aqueous solution is preferably prepared in a concentration of 1.7 mM or less, from the viewpoint of avoiding the aggregation of composite particles.

Test Example 3

An aqueous solution including a composite particle of sodium hyaluronate and a cationic polymer that was each of a primary amine and a quaternary ammonium was prepared in a similar manner as in Test Example 1. The primary amine and the quaternary ammonium are shown in Table 4.

TABLE 4

| Series of cationic group | Component name |
| --- | --- |
| Primary amine | Polylysine |
| | Protamine |

TABLE 4-continued

| Series of cationic group | Component name |
|---|---|
| Quaternary ammonium | Cationized cellulose Diallyldimethylamine hydrochloride polymer |

By adding a PBS buffer solution constituted of the ions that are universally found in the living body into an aqueous solution of the prepared composite particles, it was investigated how the composite particles under the environment imitating the inside environment of the living body behaved.

Specifically, PBS was added into an aqueous solution of the prepared composite particles, and the particle diameter of a composite particle in the aqueous solution was measured in a similar manner as in Test Example 2. The results are shown in FIG. 1.

As shown in FIG. 1, the particle diameter of the composite particle of sodium hyaluronate and the diallyldimethylamine hydrochloride polymer or cationized starch that was quaternary ammonium was increased with the addition of PBS.

On the other hand, the composite particle of sodium hyaluronate and the protamine or polylysine that was a primary amine became in a state that the particle diameter was not able to be almost measured when the addition amount of PBS was 100% (the same environment as that of the inside of the skin).

These results indicate that a composite particle of an anionic polymer and a cationic polymer that is a primary to tertiary amine other than the quaternary disintegrates under the environment of the living body such as the inside of the skin.

That is, the results indicate that the composite particle disintegrates after reaching the inside of the skin even while having skin permeability, and has a property of diffusing the polymer that is a constituent element.

Test Example 4

An emulsion preparation having the formulation shown in Table 5 was prepared. That is, an oil phase was charged in an aqueous phase while stirring the aqueous phase with a homomixer, and an emulsion preparation was obtained.

As the fluoresceinamine-labeled sodium hyaluronate, one that has an average molecular weight of 1.2 million and is manufactured by Iwai Chemicals Co. Ltd. was used. In this regard, the fluoresceinamine-labeled sodium hyaluronate can be synthesized in accordance with the method described in a literature of J Gene Med 2008; 10: 70-80.

Further, the aqueous phase component was prepared by stirring and mixing a fluoresceinamine-labeled sodium hyaluronate aqueous solution and a polylysine aqueous solution first, adding a citric acid solution into the obtained mixture, and then charging other aqueous components in the resultant mixture.

TABLE 5

| | | Mixing ratio (%) | |
|---|---|---|---|
| | | Example 7 | Comparative Example 1 |
| Aqueous phase | Fluoresceinamine-labeled sodium hyaluronate 1.65 mM aqueous solution | 33 | 33 |
| | Polylysine 1.32 mM aqueous solution | 27 | 0 |
| | Citric acid 1% aqueous solution | 1 | 0 |
| | Acrylic acid-alkyl methacrylate copolymer | 0.25 | 0.25 |
| | 1,3-Butylene glycol | 10 | 10 |
| | Sodium hydroxide | 0.1 | 0.1 |
| | Pure water | 3.65 | 31.65 |
| Oil phase | Diisopropyl adipate | 25 | 25 |

A human skin piece (Biopredic International) was attached to a vertical diffusion cell having an effective permeation area of 1.77 cm$^2$, and 4 mL of PBS was applied to the receiver side (dermal side). After that, 1 mL of each of the preparations of Example 7 and Comparative Example 1 was applied to the donor side and the treatment was performed for 24 hours.

the treated skin was recovered, the excessive preparation on the skin surface layer was washed away with pure water several times, the washed skin surface layer was homogenized in a 50% methanol aqueous solution, and then the homogenized skin surface layer was subjected to centrifugation (15400×g, at 25° C. for 5 minutes) to obtain a skin extract.

Figure 2:
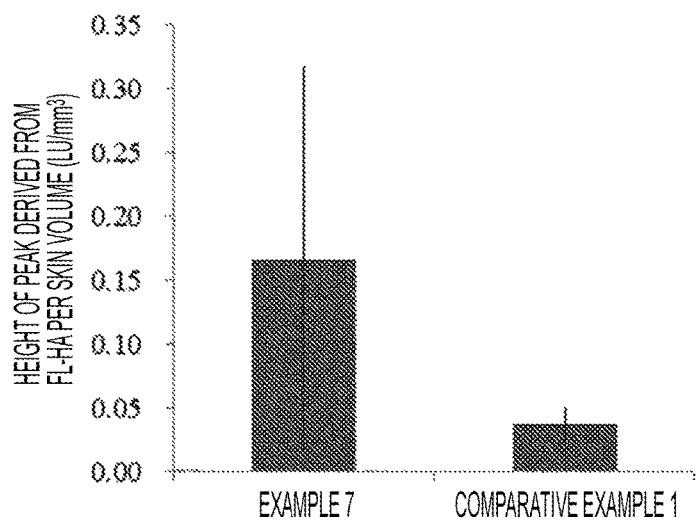
FIG. 2 is a graph showing the quantitative analysis results by HPLC of the skin extracts to which a composite particle-mixed preparation and a composite particle-free preparation was applied, respectively.

The skin extract obtained above and a standard aqueous solution of fluoresceinamine-labeled sodium hyaluronate alone were analyzed by HPLC under the following conditions. In FIG. 2, the measurement results of the fluorescence intensity in the skin extract to which each of the preparations of Example 7 and Comparative Example 1 was applied are shown. In this regard, the fluorescence was calculated from only ones that have peaks consistent with the peak derived from the fluoresceinamine-labeled sodium hyaluronate obtained as a result of analyzing the above-described standard aqueous solution.

Analyzer: Agilent 1260
Column: YMC-Pack Diol-300, 300×8.0 mm I.D., S-5 μm, 30 nm
Mobile phase: 10 mM ammonium acetate/methanol=80/20
Flow rate: 1.0 mL/min
Temperature: 40° C.
Wavelength: $\lambda_{ex}$=494 nm, $\lambda_{em}$=521 nm In addition, a skin extract to which the preparation of Example 7 was applied, a standard aqueous solution of a composite particle containing fluoresceinamine-labeled sodium hyaluronate and polylysine, and a standard aqueous solution of fluoresceinamine-labeled sodium hyaluronate alone were analyzed by FFF under the following conditions.

Figure 3:
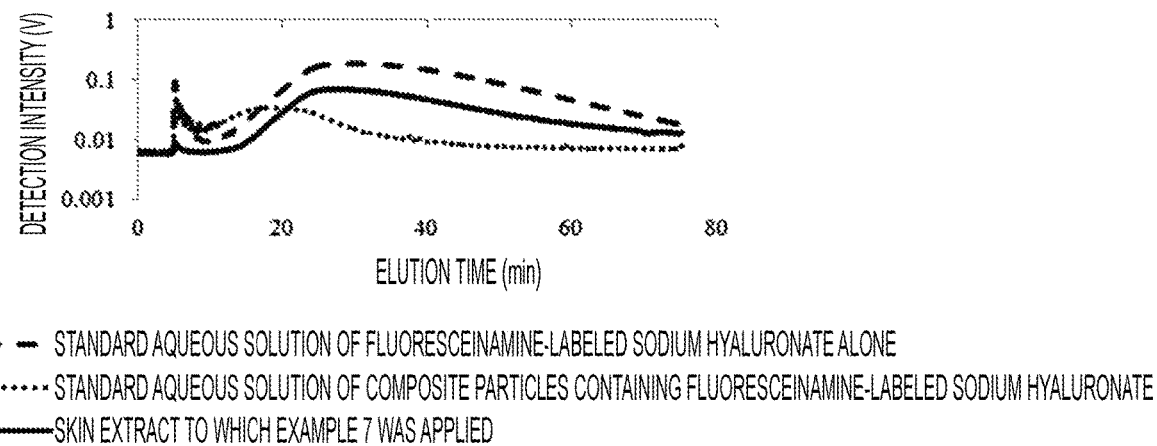
FIG. 3 is a chart showing the results of FFF analysis of a skin extract to which a composite particle-mixed preparation was applied, a standard aqueous solution of composite particles containing the fluoresceinamine-labeled sodium hyaluronate of which the concentration is known, and a standard aqueous solution of the fluoresceinamine-labeled sodium hyaluronate alone.

Analyzer: AF 2000MF Flow FFF System (AF4)
Separation channel: AF 2000 Analytical channel (AF4) 350 μm
Mobile phase: 10 mM ammonium acetate/methanol=80/20
Detection flow rate: 0.5 mL/min
Cross flow rate: 1.0 mL/min
Wavelength: $\lambda_{ex}$=494 nm, $\lambda_{em}$=521 nm As shown in FIG. 3, the elution time-intensity curves of the skin extract to which the preparation of Example 7 was applied and the standard aqueous solution of fluoresceinamine-labeled sodium hyaluronate alone are almost consistent with each other.

These results indicate that a composite particle including fluoresceinamine-labeled sodium hyaluronate and polylysine disintegrates after permeating the skin, and releases hyaluronan in a non-aggregation state into the skin.

The results of Test Examples 3 and 4 indicate that a composite particle of an anionic polymer and a cationic polymer that is a primary to tertiary amine can introduce an anionic polymer in the same state as that of an endogenous anionic polymer (such as hyaluronan) to the inside of the skin, and can improve the barrier function of the skin.

Second Aspect of the Invention

A hyaluronan aqueous solution, a peptide aqueous solution of each of polylysine, oligopeptide-20, and a water-soluble collagen were separately prepared. In this regard, each of the aqueous solutions was prepared so that the hyaluronan aqueous solution was 80.2 µg/mL, the polylysine aqueous solution was 24.0 µg/mL, the oligopeptide-20 aqueous solution was 88.2 µg/mL, and the water-soluble collagen aqueous solution was 21.87 µg/mL.

Next, a mixture solution was prepared by adding each of the peptide aqueous solutions dropwise into the hyaluronan aqueous solution while stirring. At this time, each of the peptide aqueous solutions was added dropwise into the hyaluronan aqueous solution in a volume ratio of the peptide aqueous solution to the hyaluronan aqueous solution of 0.8 to 1. After that, into each of the prepared mixture solutions, a 1 to 3% citric acid aqueous solution was added little by little to adjust the pH to the values shown in Tables 6 to 8.

hyaluronan and peptide formed in the same solution was measured. The results are shown in Tables 6 to 8.

Further, on the basis of the results of the above measurement, results obtained by evaluating the composite particle formed in each of the mixture solutions on a three-point scale in accordance with the following criteria are also shown in Tables 6 to 8.

(Evaluation Criteria for Presence or Absence of Formation of Fine Composite Particle)

○: Formation of a particle having a particle diameter of less than 300 nm
Δ: Formation of a particle having a particle diameter of 300 nm or more and less than 500 nm
x: No formation of a particle As shown in Table 6, with respect to the combination of hyaluronan and polylysine, it was confirmed that a composite particle having a minute particle diameter was formed even when the pH of the mixture solution was in the vicinity of the neutrality. However, when the mixture solution was in a pH range of 5.15 to 5.64, a fine composite particle was not formed.

Further, as shown in Tables 7 and 8, with respect to the composite particle of hyaluronan and oligopeptide-20, and the composite particle of hyaluronan and a water-soluble collagen, when the pH of the mixture solution was in a range of larger than 5, a fine composite particle was not formed.

On the other hand, as shown in Tables 6 to 8, even in any of the peptides, in case where the pH of the mixture solution

TABLE 6

Hyaluronan/polylysine fine particle system

| | pH | | | | | | | | | | | |
|---|---|---|---|---|---|---|---|---|---|---|---|---|
| | 8.9 | 7.46 | 6.68 | 6.34 | 5.64 | 5.39 | 5.15 | 4.31 | 4.14 | 3.99 | 3.85 | 3.71 |
| Particle diameter (nm) | — | 178.3 | 176.8 | 185.8 | 780 | 1791.2 | 2420.1 | 490.6 | 223.4 | 195.5 | 192.5 | 189.6 |
| Fine particle formation | X | ○ | ○ | ○ | X | X | X | Δ | ○ | ○ | ○ | ○ |

TABLE 7

Hyaluronan/oligopeptide-20 fine particle system

| | pH | | | | |
|---|---|---|---|---|---|
| | 5.27 | 3.35 | 3.13 | 2.79 | 2.78 |
| Particle diameter (nm) | — | 146.7 | 235 | 263.6 | 229.8 |
| Fine particle formation | X | ○ | ○ | ○ | ○ |

TABLE 8

Hyaluronan/water-soluble collagen fine particle system

| | pH | | |
|---|---|---|---|
| | 5.55 | 2.91 | 2.7 |
| Particle diameter (nm) | — | 197.2 | 297.6 |
| Fine particle formation | X | ○ | ○ |

The mixture solution thus prepared was measured by ELS-Z2 (manufactured by Otsuka Electronics Co., Ltd.), and the particle diameter of the composite particle of was 5 or less when the peptide is mixed with hyaluronan, a fine composite particle having a particle diameter of 500 nm or less was formed.

These results indicate that in producing a composite particle containing an anionic polymer and a peptide, it is important to mix these polymers in an aqueous solvent having a pH of 5 or less for the purpose of producing a fine composite particle.

INDUSTRIAL APPLICABILITY

The present invention can be applied to cosmetics.

The invention claimed is:

1. A composite particle, consisting of: anionic polymers; and a cationic polymer (except for chitosan) having a degree of cationization of 0.2 or more,
   the anionic polymers consist of hyaluronan, salt of hyaluronan, or combination thereof,
   the cationic polymer is one of diallyldimethylamine hydrochloride polymer, allylamine hydrochloride polymer, diallylamine hydrochloride polymer, methyl diallylamine hydrochloride polymer, acrylamide-diallyldimethylamine hydrochloride copolymer, arginine/lysine oligopeptide, polylysine, and protamine,
   an average particle diameter of the composite particle is 100 nm to 500 nm, and a mass ratio of the anionic polymers to the cationic polymer in the composite particle is 10:1 to 1:10.

2. A composition for skin external application, comprising the composite particle according to claim 1.

3. The composite particle according to claim 1, wherein the composite particle is produced by separately preparing an aqueous solution containing only the anionic polymers (A) and an aqueous solution containing only the cationic polymer (B), and these aqueous solutions are mixed with each other.

* * * * *